United States Patent

Lantzsch

[11] 4,113,969
[45] Sep. 12, 1978

[54] PREPARATION OF 2,2-DIMETHYL-3-(2,2-DIHALOGENOVINYL)-CYCLOPROPANE-1-CARBOXYLIC ACID ESTERS

[75] Inventor: Reinhard Lantzsch, Cologne, Germany

[73] Assignee: Bayer Aktiengesellschaft, Leverkusen, Germany

[21] Appl. No.: 795,588

[22] Filed: May 10, 1977

[30] Foreign Application Priority Data

May 28, 1976 [DE] Fed. Rep. of Germany ....... 2623848

[51] Int. Cl.² ............................................. C07C 51/38
[52] U.S. Cl. .................................................. 560/124
[58] Field of Search ........................................ 560/124

[56] References Cited

U.S. PATENT DOCUMENTS

| 3,658,879 | 4/1972 | Julia | 260/468 H |
| 4,000,180 | 12/1976 | Punja | 260/468 H |

*Primary Examiner*—James O. Thomas, Jr.
*Assistant Examiner*—Michael Shippen
*Attorney, Agent, or Firm*—Burgess, Dinklage & Sprung

[57] ABSTRACT

In the preparation of a 2,2-dimethyl-3-(2',2'-dihalogenovinyl)-cyclopropane-1-carboxylic acid ester of the formula

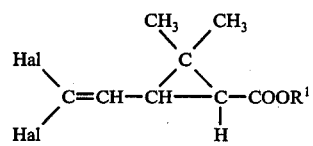

in which
Hal is halogen, and
$R^1$ is alkyl with 1 to 4 carbon atoms, by heating a 2,2-dimethyl-3-(2',2'-dihalogenovinyl)-cyclopropane-1,1-dicarboxylic acid ester of the formula

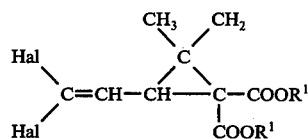

in an inert organic diluent, the improvement which comprises including a base in the diluent. Advantageously the base is 1,5-diazabicyclo[4.3.0]non-5-ene, 1,8-diazabicyclo[5.4.0]-undec-7-ene, triethylene diamine or quinuclidine and is employed in at least an equimolar amount with respect to the diester. The diluent is advantageously a hydrocarbon, a halogenated hydrocarbon or a high-boiling ether. The products are known intermediates for making insecticides.

5 Claims, No Drawings

PREPARATION OF 2,2-DIMETHYL-3-(2,2-DIHALOGENOVINYL)-CYCLOPROPANE-1-CARBOXYLIC ACID ESTERS

The present invention relates to an unobvious process for the preparation of certain 2,2-dimethyl-3-(2',2'-dihalogenovinyl)-cyclopropane-1-carboxylic acid esters, which are known.

It has been disclosed in German Published Specification DOS No. 2,536,145 that a 2,2-dimethyl-3-(2',2'-dichlorovinyl)-cyclopropane-1-carboxylic acid ester can be prepared from a 2,2-dimethyl-3-(2',2'-dichlorovinyl)-cyclopropane-1,1-dicarboxylic acid ester by heating the diester to 175° C in a mixture of dimethylsulphoxides, water and sodium chloride for a prolonged period.

However, when this reaction is carried out it is necessary to use an inert gas atmoshpere. Moreover, the use of the expensive solvent dimethylsulphoxide is not very advantageous since the reaction has to be carried out in the presence of water and the solvent therefore cannot be reused. Furthermore, dimethylsulphoxide partly decomposes at the temperatures employed. Moreover, the yields from the known process are unsatisfactory; they are about 15–20%.

The present invention now provides a process for the preparation of a 2,2-dimethyl-3-(2',2'-dihalogenovinyl)-cyclopropane-1-carboxylic acid ester of the general formula

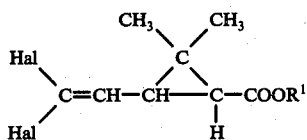

is which
Hal represents halogen and
$R^1$ represents alkyl with 1 to 4 carbon atoms, in which a 2,2-dimethyl-3-(2',2'-dihalogenovinyl)-cyclopropane-1,1-dicarboxylic acid ester of the general formula

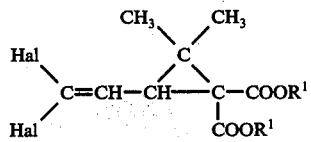

in which Hal and $R^1$ have the abovementioned meanings, is heated in the presence of an inert organic diluent and in the presence of a base.

Bases which can be used are bicyclic amidines of the general formula

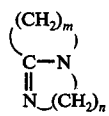

in which
m represents an integer from 3 to 7 and
n represents an integer from 2 to 4, and also tertiary amines of the general formula

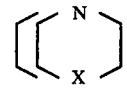

in which X represents N or CH.

The process according to the invention has a number of advantages. Thus, the use of dimethylsulphoxide as the solvent can be dispensed with since the reaction according to the invention can be carried out in the customary inert organic diluents. After removal of the reaction products, these diluents can be re-used. Moreover, it is not necessary to work under an inert atmosphere when carrying out the reaction according to the invention. Furthermore, it has proved possible to increase the yields of the desired monoester of the formula (I) by the use of the reaction according to the invention. In addition, when the reaction according to the invention is used, the trans-isomer of the monoester of the general formula (I) is preferentially obtained. This is an advantage since the trans-isomeric compounds lead to more active end products.

The process according to the invention can be carried out by heating dicarboxylic acid esters of the general formula (II) together with a base in an inert organic solvent up to the boiling point of the mixture, e.g. preferably about 80 to 250° C and especially about 130 to 250° C. Bases which can be employed according to the invention are bicyclic amidines, such as 1,5-diaza-bicyclo[4.3.0]non-5-ene and 1,8-diaza-bicyclo[5.4.0]undec-7-ene. These amidines are known and can be prepared by cyclization of corresponding N-(aminoalkyl)-lactams in the presence of acid catalysts according to the disclosure of German Published Specification DAS No. 1,545,855. Tertiary amines, such as triethylenediamine or quinuclidine, can also be employed as based.

Inert organic diluents which can be used are hydrocarbons which are liquid at the reaction temperature, especially aromatic hydrocarbons such as toluene, o-, m- or p-xylene or a technical grade mixture of xylenes, trimethylbenzene and ethylbenzene; halogenated hydrocarbons, such as chlorobenzene and o-dichlorobenzene; and high-boiling ethers, e.g. boiling above about 80° C at atmospheric pressure, such as anisole, and lower aliphatic polyethers such as diethylene glycol dimethyl ether, diethylene glycol diethyl ether and the dimethyl ether of 1,3-propanediol Xylenes and the technical grade mixtures of xylenes are particularly preferred as diluents.

The basic catalyst is usually employed in an equimolar amount or in excess but can also be employed in amounts less than the equimolar amount. In order to achieve a rapid course of reaction, it is advisable to employ an excess and subsequently to recover the basic catalyst.

The most advantageous reaction times are generally between one and twenty hours.

After the reaction has ended, ice-water and, optionally, a water-immiscible solvent, such as ether or petroleum ether, are added to the reaction mixture and the resulting mixture is acidified. Concentrated hydrochloric acid is preferably used for acidifying. The organic phase is separated off from the aqueous phase and subjected to distillation. Unconverted starting material and purified solvent can be recovered in this way and both can be re-employed to carrying out the reaction according to the invention. An alkali metal hydroxide is added to the aqueous phase and the basic catalyst is recovered in the customary manner by subsequent extraction with an organic diluent.

The dicarboxylic acid esters of the formula (II) which are used as starting materials are the subject of German Patent Application No. P 2,606,635. They may be obtained analogously to the process described in that application, for example by reacting 3-methyl-3-chlorobut-1-ene with diethyl malonate to give diethyl dimethylpropenyl malonate, to the double bond of which carbon tetrachloride is added on in the presence of benzoyl peroxide as the catalyst, and cyclizing the resulting diethyl 1,1-dimethyl-2,4,4,4-tetrachlorobutylmalonate by heating with sodium ethylate in ethanol to give diethyl 2,2-dimethyl-3-(2',2'-dichlorovinyl)-cyclopropane-1,1-dicarboxylate.

The 2,2-dimethyl-3-(2',2'-dihalogenvinyl)-cyclopropane-1-carboxylic acid esters which can e obtained when the reaction according to the invention is carried out are valuable intermediates for the preparation of highly effective insecticidal compounds described in German Published Specification DOS Nos. 2,326,077, 2,418,950, 2,436,178 and 2,439,177.

The manner in which the process according to the invention may be carried out is illustrated by the following preparative examples.

EXAMPLE 1

13 g of diethyl 2,2-dimethyl-3-(2',2'-dichlorovinyl)-cyclopropane-1,1-dicarboxylate were dissolved in 50 g of o-xylene and 20 g of 1,5-diaza-bicyclo[4.3.0]non-5-ene were added. The mixture was then heated to the boil for 8 hours. After cooling, ice-cold dilute hydrochloric acid was added, so that a neutral or weakly acid pH value resulted. The organic phase was separated off and dried with $Na_2SO_4$ and the xylene was distilled off in vacuo (boiling point = 35° – 40° C/12 mm Hg). The residue weighed 12.5 g. Fractional distillation gave 4.7 g of 2,2-dimethyl-3-(2',2'-dichlorovinyl)-cyclopropane-1-carboxylic acid ethyl ester, of which 30% was in the cis form and 70% was in the trans form. The boiling point was 65° – 72° C/0.3 mm Hg. The nuclear magnetic resonance spectrum agreed with that given in the literature. 6.5 g of the starting material were recovered. The yield was thus 92%.

EXAMPLE 2

13 g of diethyl 2,2-dimethyl-3-(2',2'-dichlorovinyl)-cyclopropane-1,1-dicarboxylate were dissolved in 50 g of xylene (technical grade) and 30 g of 1,8-diaza-bicyclo[5.4.0]undec-7-ene were added. The mixture was then heated to the boil for 8 hours. After cooling, ice-cold dilute hydrochloric acid was added so that a neutral or weakly acid pH value resulted. The organic phase was separated off and dried with $Na_2SO_4$ and the xylene was distilled off in vacuo. The residue weighed 12.2 g. Fractional distillation gave 3.4 g of ethyl 2,2-dimethyl-3-(2',2'-dichlorovinyl)-cyclopropane-1-carboxylate and also 8.0 g of recovered starting material. The yield was thus 87%.

EXAMPLE 3

13 g of diethyl 2,2-dimethyl-3-(2',2'-dichlorovinyl)-cyclopropane-1,1-dicarboxylate were dissolved in 50 g of o-xylene and 20 g of triethylenediamine were added. The mixture was then heated to the boil for 6 hours. After cooling, ice-cold dilute hydrochloric acid was added so that a neutral or weakly acid pH value resulted. The organic phase was separated off and dried with $Na_2SO_4$ and the xylene was distilled off in vacuo. The residue weighed 10 g. Fractional distillation gave 2 g of ethyl 2,2-dimethyl-3-(2',2'-dichlorovinyl)-cyclopropane-1-carboxylate as well as 6.7 g of recovered starting material. The yield was thus 40%.

EXAMPLE 4

77 g (0.25 mol) of diethyl 2,2-dimethyl-3-(2',2'-dichlorovinyl)-cyclopropane-1,1-dicarboxylate were dissolved in 300 g of o-xylene and 150 g of 1,5-diazabicyclo[4.3.0]non-5-ene were added. The mixture was then heated to the boil for 12 hours. After cooling, the mixture was rendered weakly acid with ice-cold dilute hydrochloric acid. The organic phase was separated off and the aqueous phase was extracted twice more by shaking with methylene chloride. The combined organic phases were washed with sodium chloride solution and then with water and dried with $Na_2SO_4$. Fractional distillation gave 36.6 g of ethyl 2,2-dimethyl-3-(2',2'-dichlorovinyl)-cyclopropane-1-carboxylate in the form of a cis/trans mixture in which the trans form greatly predominated.

For comparison with the above, an embodiment of the process which is known from German Published Specification DOS No. 2,536,145 for splitting off the alkoxycarbonyl group from a diester of the general formula (II) with the aid of dimethylsulphoxide, water and sodium chloride was carried out as follows:

Comparison Example A

A mixture of diethyl-2-(2',2'-dichlorovinyl)-3,3-dimethyl-1,1-cyclopropane-dicarboxylate (5.0 g), sodium chloride (0.95 g), dimethylsulphoxide (12.0 ml) and water (0.6 ml) was heated to 175° C under a nitrogen atmosphere and kept at this temperature for 9 hours. At the end of this time, the mixture was cooled to room temperature and poured into water (50 ml). The mixture was extracted with petroleum ether (boiling point 60° to 80° C) and the extracts were dried over anhydrous magnesium sulphate. After removing the solvent by evaporating under reduced pressure, the residual oil was purified by distillation and ethyl 2-(2',2'-dichlorovinyl)-3,3-dimethyl-cyclopropane-carboxylate was obtained as a colorless liquid (boiling point 102° C/13.3 Pa) in a yield of 15–20% of theory. The identity of the compound was confirmed by comparing the IR spectrum with that of an authentic sample. The mixture contained the trans isomer and the cis isomer in a ratio of 55 to 45.

It will be appreciated that the instant specification and examples are set forth by way of illustration and not limitation, and that various modifications and changes may be made without departing from the spirit and scope of the present invention.

What is claimed is:

1. In the preparation of a 2,2-dimethyl-3-(2',2'-dihalogenovinyl)-cyclopropane-1-carboxylic acid ester of the formula

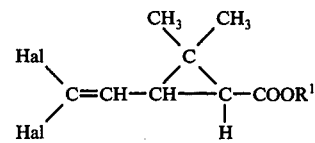

in which

Hal is halogen, and
R₁ is alkyl with 1 to 4 carbon atoms, by heating a 2,2-dimethyl-3-(2',2'-dihalogenovinyl)-cyclopropane-1,1-dicarboxylic acid ester of the formula

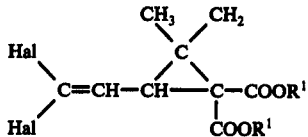

in an inert organic diluent, the improvement which comprises employing as the diluent a hydrocarbon, halogenated hydrocarbon or high-boiling ether which is liquid at the reaction temperature, and including in the diluent a base which is a bicyclic amidine of the formula

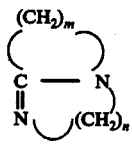

in which
   m is an interger from 3 to 7, and
   n is an interger from 2 to 4, or a tertiary amine of the formula

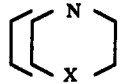

in which
   X is N or CH.

2. A process according to claim 1, in which the base is 1,5-diazabicyclo[4.3.0]non-5-ene or 1,8-diazabicyclo[5.4.0]-undec-7-ene.

3. A process according to claim 1, in which the inert organic diluent is at least one xylene.

4. A process according to claim 1, in which the base is employed in at least an equimolar amount with respect to the diester.

5. A process according to claim 4, in which the base is 1,5-diazabicyclo[4.3.0]non-5-ene, 1,8-diazabicyclo[5.4.0]undec-7ene, triethylenediamine or quinuclidine.

* * * * *